United States Patent [19]
Segalowitz

[11] Patent Number: 5,176,619
[45] Date of Patent: Jan. 5, 1993

[54] HEART-ASSIST BALLOON PUMP WITH SEGMENTED VENTRICULAR BALLOON

[76] Inventor: Jacob Segalowitz, 279 S. Beverly Dr., #1036, Beverly Hills, Calif. 90212

[21] Appl. No.: 347,674

[22] Filed: May 5, 1989

[51] Int. Cl.$^5$ .............................................. A61M 1/10
[52] U.S. Cl. ........................................ 600/18; 600/17; 600/16
[58] Field of Search ................. 600/16, 17, 18; 623/3; 604/96–101, 104

[56] References Cited

U.S. PATENT DOCUMENTS

| | | | |
|---|---|---|---|
| 388,510 | 8/1888 | Terrell | 604/96 |
| 2,687,131 | 9/1952 | Raiche | 604/101 |
| 3,509,884 | 5/1970 | Bell | 604/101 |
| 3,568,659 | 3/1971 | Karnegis | 600/18 |
| 4,430,076 | 2/1984 | Harris | 604/96 |
| 4,619,247 | 10/1986 | Inoue et al. | 604/96 |
| 4,627,837 | 12/1986 | Gonzalo | 604/101 |
| 4,689,041 | 8/1987 | Corday et al. | 604/53 |
| 4,861,330 | 8/1989 | Voss | 600/18 |
| 5,021,045 | 6/1991 | Buckberg et al. | 604/96 |

FOREIGN PATENT DOCUMENTS 1003845 3/1983 U.S.S.R. ............................... 600/16

Primary Examiner—Kyle L. Howell
Assistant Examiner—Kennedy J. Schaetzle
Attorney, Agent, or Firm—Flehr, Hohbach, Test, Albritton & Herbert

[57] ABSTRACT

A heart-assist device which includes a flexible catheter carrying at least a ventricular balloon, such balloon corresponding in size and shape to the size and shape of the left ventricle in the heart being assisted, the ventricular balloon being progressively inflated creating a wave-like pushing effect and deflated synchronously and automatically by means of a control console which responds to heart signals from the catheter or elsewhere, the catheter optionally also carrying an aortic inflated and deflated automatically and synchronously (but in opposite phase) with the ventricular balloon by means of the control console to ensure high speed inflation-deflation.

6 Claims, 1 Drawing Sheet

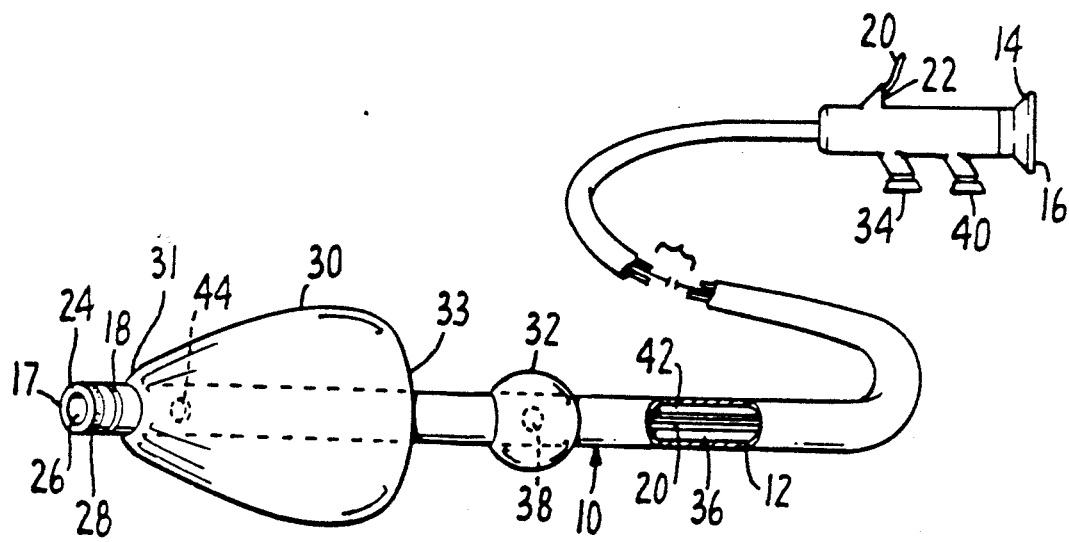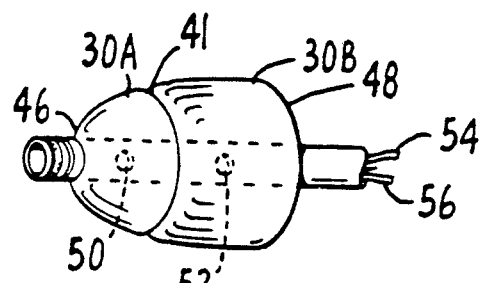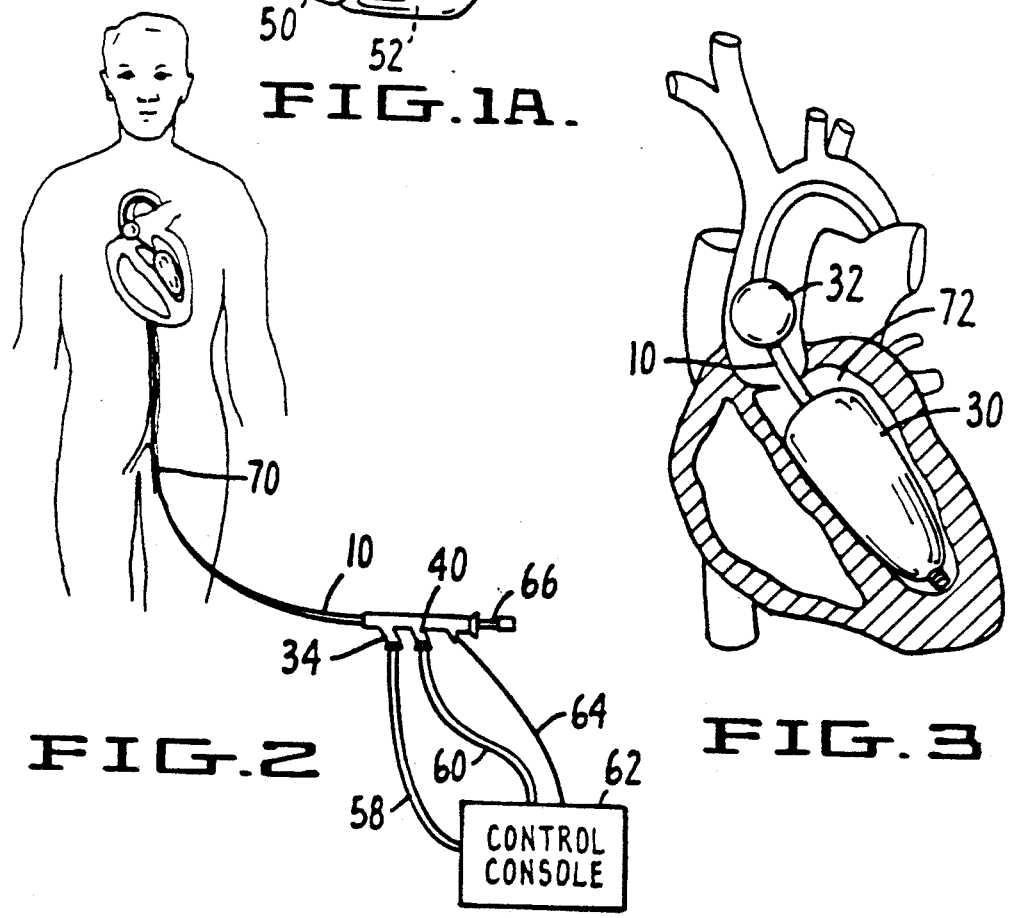
FIG.1.
FIG.1A.
FIG.2
FIG.3

HEART-ASSIST BALLOON PUMP WITH SEGMENTED VENTRICULAR BALLOON

BACKGROUND OF THE INVENTION

1. Field of the Invention

This invention relates to heart-assist devices and, more particularly, to such devices incorporating balloon pumps.

2. Prior Art

During the past thirty years there has been an ever-increasing frequency of heart surgery and greater study and knowledge of the functions of the heart. One of the product groups which has resulted from this increased activity in the knowledge of the function of the heart has been what are known as temporary circulatory-assist devices. The purpose of such devices is to stabilize, hemodynamically, a failing circulatory system resulting from a failure in the pumping action of the heart. Beneficial results have been realized by the use of heart-assist devices in patients with cardiogenic shock and in severe acute myocardial ischemia. Further, in the critical moments before or after a heart transplantation or after open heart surgical procedures, temporary support of the cardiocirculatory system is crucial.

These heart-assist devices are intended to give the heart muscle the necessary time to rest and optionally to recover.

The best known of the circulatory-assist devices is the intra-aortic balloon with its counterpulsation capability. With the development of percutaneous techniques for the balloon insertion (for example, through the femoral artery) it is possible to give immediate response to a critical heart condition. However, with the intra-aortic balloon, the cardiac output is increased approximately thirty to forty percent. It is clear that a more effective heart-assist device is necessary, particularly in the first moments of intervention, to prevent deterioration of the circulatory system of the patient.

Therefore, it is an object of this invention to provide a heart-assist device which is compact, is easily handled by a single specialist, is completely a traumatic both to the ventricular chamber and to the blood volume constituents, and is highly effective so as to achieve nearly normal physiological conditions during its use.

SUMMARY OF THE INVENTION

The present invention comprises a cardiac-assist, double balloon catheter for pumping blood from the left ventricle of the heart to the aorta synchronically with the left ventricle systole and diastole timing.

A flexible catheter having a central hollow passage carries two balloons. The first (distal) balloon, the ventricular balloon, is positioned at the distal tip of the catheter. The second proximal the aortic balloon, is positioned closer to the proximal end of the catheter. The double balloon pump catheter is introduced percutaneously through a peripheral artery and negotiated into the left ventricle of the heart by means of a flexible cardiac guide wire.

The ventricular balloon is larger and longer is size than the aortic balloon, and when inflated fills the chamber of the left ventricle of the heart almost completely. The ventricular balloon preferably has the shape and size of the left ventricle of the heart. The aortic balloon is round or elongated in shape and when inflated fits the size of the aorta.

The distal tip of the catheter may have a sensor for detecting the electrocardiographic activity of the heart. That sensor has one or more conductors which may be carried in the wall of the catheter to a connector at the proximal end of the catheter. That connector is adapted for connection to an external inflator-deflator which, in response to the electrical activity of the hear, inflates and deflates the ventricular and aortic balloons in synchronized fashion with the proper phase relationship. The heart-signal for controlling inflation and deflation, instead of being derived from the sensor on the catheter, may be derived from standard electrocardiographic devices.

The control console assures that the aortic balloon is inflated only during diastole and is deflated during systole. Conversely, the ventricular balloon is inflated during systole and deflated during diastole.

When the ventricular balloon is deflated, blood flows into the left ventricle from the left atrium.

The timing of the inflation and deflation of each balloon is related to the heart cycle as represented by the electrical signals from the heart. The aortic balloon is inflated immediately after the aortic valve closes so that during diastole the aortic pressure is increased. This increases aortic perfusion. The deflation of the coronary balloon occurs just before the start of systole so that aortic impedance to the left ventricular ejection is decreased.

The ventricular balloon is immediately inflated after closure of the mitral valve with the start of systole. The inflation progresses rapidly from the distal part of the ventricular balloon towards its proximal end so that a wave-like "pushing" effect is achieved during the rapid inflation, thus forcing the blood from the left ventricle of the heart through the open aortic valve into the aorta where the aortic balloon at that time is deflated. Deflation of the ventricular balloon begins just before the start of diastole with the closure of the aortic value (between the left ventricle and the aorta) so that left ventricle impedance to atrial blood flow passing during diastole through the mitral valve (between the left atrium and the left ventricle) is eliminated.

The rapid, wave-like "pushing" effect on the left ventricle blood volume has the identical effect of ejecting the blood. Since the ventricular balloon corresponds in shape and volume to the shape and almost to the entire volume of the left ventricle of the heart, the stroke-ejected blood volume (stroke output) pumped out from the left ventricle by the effect provides a potential stroke output of nearly 100 percent.

Both the ventricular balloon and the aortic balloon are inflatable and deflatable separately and independently, one from the other, from two separated inflation-deflection port connectors positions at the very proximal end of the balloon pump catheter. Such port connectors are connected to the external inflator-deflator console.

The central, open-ended lumen of the catheter is connected to a port connector positioned at the most proximal end of the catheter. Contrast solution may thereby be injected to provide the exact positioning of the balloon-pump catheter in the aorta and the left ventricle of the heart during X-ray inspection. This corresponds to current procedures during heart catheterization. The central lumen also aids in adjusting timing and synchronization when monitoring arterial pressure. The ventricular balloon and the aortic balloon may come in different volume sizes, thus making the balloon pump catheter suitable for use with optimal precision in prediatric or adult patients.

The intra-aortic balloon by itself assists circulation by approximately twenty percent. When combined with the ventricular balloon, the effectiveness of the circulation support is very close to optimal.

The manipulation of the balloon pump catheter of the present invention is simple and does not require training or equipment different from current heart catheterization techniques or equipment. Thus, the present balloon pump can be applied immediately.

BRIEF DESCRIPTION OF THE DRAWING

The invention herein and the means by which it achieves the original, new and unobvious results, can best be understood by referring to the detail description which follows, taken in conjunction with the drawing herein, in which:

FIG. 1 is an elevational view of the heart balloon pump catheter according to this invention;

FIG. 1A is an elevational view of a portion of the structure of FIG. 1 illustrating an alternate embodiment of a ventricular balloon;

FIG. 2 is a schematic the present invention in place in the heart of a patient and coupled to external control means; and FIG. 3 is an enlarged view of the invention installed in the heart of a patient.

DETAILED DESCRIPTION OF THE PREFERRED EMBODIMENTS

In FIG. 1, catheter 10 has a flexible body 12, which is hollow. At its proximal end 14, catheter 10 has a connector 16 for introduction of a contrast solution helpful in the X-ray observation of the installation location and operation of catheter 10. At distal end 17 of catheter 10 there is a sensor 18 for detecting heart action voltages whereby the synchronized inflation and deflation of the balloons associated with the catheter can be achieved by external inflation and deflation means referred to in connection with FIG. 2. Signals from sensor 18 are carried through conductor 20, which may be carried within the walls of flexible body 12. Connection 20 ultimately emerges from flexible body 12 at electrical output port 22 in flexible body 12 of catheter 10. Tip 24 of catheter 10 is open, thereby exposing lumen 26. Tip 24 may also carry an opaque marker 28 which makes possible accurate location of tip 28 by X-ray means.

Catheter 10 carries thereon, in sealed fashion, left ventricular balloon 30 and aortic balloon 32. Aortic port 34 in catheter body 12 is coupled by means of tube 36 to inflation aperture 38 within the confines of aortic balloon 32. Ventricular port 40 is coupled by means of tube 42 to inflation aperture 44 which is within the confines of ventricular balloon 30. The shape of ventricular balloon 30 is of particular note. When inflated, ventricular balloon 30 has a shape which may be technically described as approximately a frusto-conical shape. However, the shape may more practically be descried as the shape of the left ventricle when filled with blood. The shape and size of ventricular balloon 30 is, of course, intended to fully discharge blood from the left ventricle at the appropriate moment in the heart cycle. By reason of its tapered shape, the inflation of ventricular balloon 30 commences at narrower distal end 31 of balloon 30, and progresses toward proximal end 33, terminating in the base or wide end of ventricular balloon 30 with the result that there is a rapid, wave-like "pushing" effect on the left ventricular blood volume and an ejection of blood from the left ventricle to nearly 100 percent of the volume of the left ventricle.

As shown in FIG. 1A, it is possible to segment ventricular balloon 30 into two or more segments 30A and 30B. This will ensure the progressive inflation of the overall balloon from distal end 46, to proximal end 48, thus ensuring the aforementioned pushing action upon the blood in the left ventricle. For full control, separate inlet ports 50 and 52 with associated inflating medium input and output tubes 54, 56, respectively, are provided. With this two-segment configuration an additional portion will have to be provided on catheter 10, and the control console shown in FIG. 2 will have to have an additional inflation-deflation port with an associated control circuitry, all of which are controlled in response to heart-signals derived either from the sensor 18 or from an independent source of electrical heart-signals.

Turning to FIG. 2, the heart balloon pump catheter according to this invention is shown diagrammatically, in place in a human heart. Aortic ventricular ports 34, 40 are shown coupled by tubes 58, 60, respectively, to control console 62. Electrocardiographic signals are received by control console 62 through conductor 64 and synchronized. High speed, inflation and deflation of the respective balloons is achieved by utilizing an inflating medium which has a very low atomic weight. Control console 62 is an extension of the control console commonly used today in connection with intra-aortic balloons.

The manipulation and insertion of the balloon pump catheter according to this invention is simple and does not require training or equipment different from that currently in use. Catheter 10 may be introduced through femoral artery 70 in the groin of the patient. Tube 66 having connector 16 is available for introduction of contrast fluid. As can be seen in FIG. 3, when the catheter 10 is fully inserted, ventricular balloon 30, which is a the distal end of catheter 10, is placed at the apex of the left ventricle 72 of heart. As has been indicated, inflation of ventricular balloon 30 begins at the most remote portion of the balloon which is immediately adjacent the apex of left ventricle 72, and inflation progresses toward the base of ventricular balloon 30. Thus blood is pumped out of left ventricle 72 into. Aortic, the aortic balloon 32 is collapsed or deflated at moment the ventricular balloon 30 is inflated. The fast, progressive inflation of ventricular balloon 30 from the ventricle apex toward the aorta correlates exactly with the normal physiological reaction arising from ventricular muscle contraction. Thus, the blood is pumped out of the left ventricle into the aorta.

According to this invention, heart balloon pump catheter may have only the ventricular balloon, thus eliminating the aortic balloon from catheter 10. With this structure there is a single, synchronized balloon pump, i.e., the ventricular shaped and sized according to this invention. The same wave-like "pushing" ejection of blood from the left ventricle of the heart into the aorta, during systole, is achieved by way of this embodiment of the invention. Ventricular balloon 30 displaces a volume of blood equivalent to the ventricular balloon's volume, and proper synchronism is controlled by control console 62.

Experiments have shown that the inflation-deflation sequence of either ventricular balloon 30 by itself or the combination of ventricular balloon 30 and aortic balloon 32 can be achieved in approximately 0.025 seconds, i.e., in with the heart action.

It should be understood that while the captive control console has been shown as deriving its control signal from a sensor at the distal end of the catheter, other sources of the cyclical heart signals may be used to activate control console 62 and to synchronize the inflation-deflation of the balloon pumps.

Thus, the aortic balloon is inflated during diastole and is deflated during systole. Conversely, ventricular balloon 30 is inflated during systole and deflated during diastole. When ventricular balloon 30 is deflated, blood comes into the left ventricle from the left atrium of the heart for the next cycle of operation.

While particular embodiments of invention have been shown and described, it will be apparent to those skilled in the art that variations and modifications may be made therein without departing from the true scope and spirit of the invention. It is the purpose of the appended claims to cover all such variations and modifications.

I claim:

1. A heart-assist device comprising a catheter having a passage therethrough and having a distal end and a proximal end and a ventricular balloon carried by said catheter near the distal end thereof but not obstructing said passage and having an inflated size and shape approximating the size and shape of the left ventricle, when filled, of the heart of a patient whose heart is being assisted, said ventricular balloon having a proximal end and a distal end, said ventricular balloon expanding upon inflation from said distal end toward said proximal end of said ventricular balloon to create a wave-like pushing effect on blood within the left ventricle of a patient, said catheter having inflation aperture coupled into said ventricular balloon to introduce an inflating medium into said ventricular balloon yet allowing continued access through said distal end of said catheter, said ventricular balloon being frusto-conical in shape and being narrower at its distal end than at its proximal end and being generally fixed in axial length so that expansion is generally radial in direction said ventricular balloon being segmented for sequential inflation.

2. A heart-assist device comprising a catheter having a passage therethrough and having a distal end and a proximal end, a ventricular balloon carried by said catheter near the distal end thereof but not obstructing said passage and having an inflated size and shape approximating the size and shape of the left ventricle, when filled, of the heart of a patient whose heart is being assisted, said ventricular balloon having a wider proximal end and a narrower distal end, said ventricular balloon being formed so that inflation of the ventricular balloon proceeds from said distal end toward said proximal end to create a wave-like pushing effect during inflation within the left ventricle of the patient, an aortic balloon carried by said catheter closer to said proximal end of said catheter then said ventricular balloon, tube means carried by said catheter independently carrying an inflating medium to said ventricular and aortic balloons yet allowing continued access through said distal end of said catheter, said ventricular balloon being frusto-conical in shape and being generally fixed in axial length so that the expansion is generally radial in direction, said ventricular balloon being segmented.

3. A heart-assist device comprising:
a flexible catheter having a passage therethrough and having a distal end and a proximal end and
a ventricular balloon carried by said catheter near the distal end thereof but not obstructing said passage and having an inflated size and shape approximating the size and shape of the left ventricle, when filled, of the left ventricle of a patient whose heart is being assisted, said ventricular balloon having a wider proximal end and an narrower distal end, said catheter having an aperture therein in communication with the interior of the ventricular balloon and conduit means in communication with the aperture for introducing an inflating medium into the ventricular balloon, said ventricular balloon progressively expanding upon inflation by the inflating medium from said distal end toward said proximal end of said ventricular balloon to create a wave-like pushing effect on the blood within the left ventricle of a patient, wherein said ventricular balloon is frusto-conical in shape and is generally fixed in axial length so that expansion is generally radial in direction, said ventricular balloon being formed of a plurality of segments, said catheter having a plurality of apertures therein with one aperture being in communication with each segment and a plurality of conduit means with one conduit means being in communication with each aperture for introducing an inflating medium into each segment in a sequential manner for sequential inflation of the ventricular balloon.

4. A heart-assist device comprising:
a catheter having a passage therethrough and having a distal end and a proximal end;
a ventricular balloon carried by said catheter near the distal end thereof but not obstructing said passage and having in inflated size and shape approximating the size and shape of the left ventricle, when filled, of the heart of a patient whose heart is being assisted, said ventricular balloon having a wider proximal end and a narrower distal end, said ventricular balloon being formed so that inflation of the ventricular balloon proceeds from said distal end toward said proximal end to create a wave-like pushing effect during inflation within the left ventricle of a patient;
an aortic balloon carried by said catheter closer to said proximal end of said catheter than said ventricular balloon; and
tube means carried by said catheter for independently carrying an inflating medium to said ventricular and aortic balloons yet allowing continued access through said distal end of said catheter, wherein said ventricular balloon is frusto-conical in shape and is generally fixed in axial length so that expansion is generally radial in direction, said ventricular balloon being segmented.

5. A heart-assist device comprising a catheter having a passage therethrough and having a distal end and a proximal end;
a balloon carried by said catheter proximate the distal end thereof and having an inflated size and shape approximating the size and shape of the left ventricle, when filled, of the heart of a patient whose heart is being assisted; and
inflated means carried by said catheter for carrying an inflating medium to said ventricular balloon, said ventricular balloon being segmented.

6. A heart-assist device comprising a catheter having a passage therethrough and having a distal end and a proximal end;

a ventricular balloon carried by said catheter proximate the distal end thereof and having an inflated size and shape approximating the size and shape of the left ventricle, when filled, of patient whose heart is being assisted;

an aortic balloon carried by said catheter more proximate to said proximal end of said catheter than said ventricular balloon;

tube means carried by said catheter for carrying an inflating medium to said ventricular and aortic balloons, respectively and independently, said ventricular balloon being segmented.

* * * * *